United States Patent [19]

Day et al.

[11] Patent Number: 5,610,019
[45] Date of Patent: Mar. 11, 1997

[54] METHODS OF DETECTING PHOSPHOLIPID TRANSFER ACTIVITY AND KITS THEREFOR

[75] Inventors: Joseph R. Day, Brier; John J. Albers, Seattle; Catherine E. Lofton-Day, Brier; Janet L. Adolphson, Mountlake Terrace, all of Wash.

[73] Assignee: ZymoGenetics, Inc., Seattle, Wash.

[21] Appl. No.: 462,733

[22] Filed: Jun. 5, 1995

Related U.S. Application Data

[62] Division of Ser. No. 176,402, Dec. 30, 1993.

[51] Int. Cl.[6] .................. C12N 9/10; C12N 9/12; C12N 11/00; C12Q 1/48
[52] U.S. Cl. .................. 435/7.1; 435/4; 435/7.4; 435/7.6; 435/7.92; 435/69.1; 435/69.6; 435/172.3; 435/183; 435/15
[58] Field of Search ............... 435/4, 7.1, 7.4, 435/7.6, 7.92, 69.1, 69.6, 172.3, 183, 15

[56] References Cited

PUBLICATIONS

Jauhiainin et al., *J. Biol. Chem.* 268: 4032–4036, 1993.
Tollefson et al., *J. Lipid Res.* 29: 1593–1602, 1989.
Albers et al., *Arteriosclerosis* 4: 49–58, 1984.
Agellon et al., *Biochemistry* 29: 1372–1376, 1990.
Nishide et al., *J. Lipid Res.* 30: 149–157, 1989.
Drayna et al., *Nature* 327: 632–634, 1987.
Tollefson et al., *Am. J. Physiol.* 255: E894–E902, 1988.
Damen et al., *Biochim. Biophys. Acta.* 712: 444–452, 1982.
Tu et al., *J. Biol. Chem.* 268(31): 23098–23105, 1993.
Tollefson et al., *Am. Heart Assoc. Monographs* 124: Abstract 4, 1986.

*Primary Examiner*—Stephen G. Walsh
*Assistant Examiner*—Elizabeth C. Kemmerer
*Attorney, Agent, or Firm*—Deborah A. Sawislak; Gary E. Parker; Debra K. Leith

[57] ABSTRACT

Isolated polynucleotide molecules encoding mammalian phospholipid transfer proteins (PLTP) and phospholipid transfer protein polypeptides are disclosed. The DNA molecules are transformed or transfected into host cells and the cells cultured to produce recombinant PLTP and PLTP polypeptides. PLTP and PLTP polypeptides may be combined with a pharmaceutically acceptable vehicle and administered to patients to regulate phospholipid transfer activity and thereby obtain a more favorable lipoprotein profile in the blood. The proteins and polypeptides may also be used within methods to measure phospholipid transfer activity or identify inhibitors of phospholipid transfer activity.

4 Claims, No Drawings

METHODS OF DETECTING PHOSPHOLIPID TRANSFER ACTIVITY AND KITS THEREFOR

This invention was made with government support under National Institutes of Health Program Project Grant number HL-30086. The government has certain rights in the invention.

This is a divisional application of co-pending application Ser. No. 08/176,402, filed Dec. 30, 1993.

BACKGROUND OF THE INVENTION

Accumulation of cholesterol in the vascular wall is believed to be a key event in the development of atherosclerosis (for review, see Ross, *Nature* 362: 801–809, 1993). Early in the development of atherosclerotic lesions, the artery walls are penetrated by cholesterol-containing atherogenic particles. These particles are believed to be derived from low-density lipoproteins (LDL) or to be minor subpopulations of sterol-rich lipoproteins. They are recognized as foreign by macrophages, which pick up the particles, integrate the cholesterol, and thereby become foam cells. Accumulation of foam cells is the first stage of fatty streak formation. These fatty streaks then enlarge through the gradual accumulation of lipid-containing macrophages and smooth muscle cells, eventually developing into fibrous plaques rich in smooth muscle cells.

The structure and activity of plasma lipoproteins have been reviewed by Gotto et al. (*Meth. in Enzymology* 128: 3–41, 1986). High-density lipoproteins (HDL) are a class of plasma lipoproteins which consist of cholesterol, cholesteryl esters, phospholipids, triglycerides, and apolipoproteins (principally apoA-I and apoA-II). HDL have been implicated in the transport of cholesterol (principally in the form of cholesteryl esters) from peripheral tissues to the liver, where the cholesterol is catabolized or excreted (Glomset, *Lipid Res.* 9: 155–167, 1968). The transfer of cholesteryl ester (CE), triglycerides (TG), and phospholipids (PL) is mediated by at least two different lipid transfer proteins, lipid transfer protein (LTP-I) (Nishide et al., *J. Lipid Res.* 30:149–158, 1989), also called cholesteryl ester transfer protein (CETP) (Drayna et al., *Nature* 327:632–634, 1987) and phospholipid transfer protein (PLTP), also called lipid transfer protein II (LTP-II) (Albers et al., *Arteriosclerosis* 4:49–58, 1984; Tollefson et al., *J. Lipid Res.* 29:1593–1602, 1988 and are incorporated herein in their entirety).

Several lines of evidence have strongly implicated CETP and PLTP as key regulators of HDL and LDL metabolism, controlling cholesterol homeostasis and the development of atherosclerosis. Studies with transgenic animals show that increased levels of CETP produce an atherogenic lipoprotein profile (increased LDL and decreased HDL) and are positively correlated with LDL cholesterol concentration and the degree of coronary artery atherosclerosis (Quinet et al., *J. Clin. Invest.* 87:1559–1566, 1991; Marotti et al., *Nature* 364:73–75, 1993). Humans with a genetic deficiency of CETP have no evidence of premature atherosclerosis and have significantly increased levels of HDL as well as reduced LDL (Inazu et al., *New Eng. J. Med.* 323:1234–1238, 1990). Evaluation of CETP-deficient individuals indicates a lipoprotein profile that is anti-atherogenic and associated with an increased life span. Together these studies provided convincing evidence that CETP is a proatherogenic protein.

Evidence suggests that CETP and PLTP act together to effect lipid transfer. CETP activity is enhanced by PLTP (Tollefson et al., ibid.) or by enriching HDL with phospholipid (Tall, *J. Lipid Res.* 27:361–367, 1986). Lipid transfer inhibitor protein modulates the activity of both transfer proteins (Nishide et al., *J. Lipid Res.* 30:149–158, 1989). Where earlier data have suggested that CETP alone was responsible for HDL interconversion (Lagrost et al., *J. Lipid Res.* 31:1569–1575, 1990), recently it has been shown that PLTP promotes the conversion of high density lipoproteins (HDL) into populations of larger and smaller particles in the absence of other lipoproteins (Jauhiainen et al., *J. Biol. Chem.* 268:4032–4036, 1993). However, while it was believed that PLTP and CETP both played roles in regulation of HDL and LDL, it appeared that there was little homology between various lipid transfer proteins (Tollefson et al., ibid. 988). The ability of PLTP to promote the conversion of HDL indicated that PLTP and CETP may act through synergistic mechanisms.

In view of the relationship between cholesterol and phospholipid transfer to cholesterol homeostasis and atherosclerosis, there is a need in the art for agents that regulate cholesterol homeostasis. However, elucidation of the interaction between CETP and PLTP in LDL and HDL phospholipid transfer has been impeded by the inability to isolate sufficient quantities of PLTP because PLTP is present only in trace amounts in vivo. Cloning of PLTP provides a means to produce larger amounts of recombinant protein. There is also a need in the art for agents that regulate levels of HDL, LDL and VLDL. In vitro measurements of components involved in phospholipid transfer are needed as diagnostics in both research and clinical settings. It is an object of the present invention to provide such agents. It is a further object of the invention to provide methods for controlling phospholipid transfer from LDL to other lipoprotein classes, and to provide pharmaceutical compositions for use within these methods. Towards these ends, the present invention provides novel polynucleotide molecules encoding a phospholipid transfer protein.

DISCLOSURE OF THE INVENTION

Broadly stated, the present invention provides isolated polynucleotide molecules encoding mammalian phospholipid transfer proteins and polypeptide fragments thereof. Within a preferred embodiment, the encoded phospholipid transfer protein is a human phospholipid transfer protein. These proteins and polypeptides may be combined with a pharmaceutically acceptable vehicle and administered to a patient to regulate lipid transfer, or may be used as standards in screening systems for identifying other molecules capable of controlling phospholipid transfer.

Within one aspect, the isolated polynucleotide molecule of the present invention is selected from the group consisting of (a) DNA molecules having a coding sequence corresponding to SEQ ID NO:1 from nucleotide 88 to nucleotide 1566, (b) SEQ ID NO:1 from nucleotide 139 to nucleotide 1566, (c) SEQ ID NO:1 from nucleotide 523 to nucleotide 1566; (d) allelic variants of (a), (b) and (c); and (e) polynucleotide molecules that specifically hybridize to (a), (b), (c) or (d).

Within another aspect of the present invention, are DNA molecules encoding the amino acid sequence of SEQ ID NO:2 from amino acid residue number 137 (Gly) to amino acid residue number 493 (Val) or an allelic variant thereof.

Within another aspect of the invention, the isolated polynucleotide molecule of the present invention comprises a polypeptide selected from the group consisting of (a) a polypeptide having the amino acid sequence of SEQ ID NO:2 from amino acid residue number 1 (Met) to amino acid residue number 493 (Val), (b) a polypeptide having the amino acid sequence of SEQ ID NO:2 from amino acid residue number 18 (Glu) to amino acid residue number 493 (Val), (c) a polypeptide having the amino acid sequence of SEQ ID NO:2 from amino acid residue number 137 (Gly) to amino acid residue number 493 (Val) and (d) allelic variants of (a), (b) or (c).

Within another aspect of the invention, polynucleotide molecules are provided that encode mammalian phospholipid transfer protein polypeptides of from 5 to 66 amino acids. Within preferred embodiments, the phospholipid transfer protein polypeptide is a human phospholipid transfer protein polypeptide. Of particular interest in this regard are polynucleotide molecules selected from the group consisting of (a) DNA molecules having a coding sequence corresponding to a sequence of at least 15 consecutive nucleotides of SEQ ID NO:1; (b) allelic variants of (a); and (c) polynucleotide molecules that specifically hybridize to (a) or (b). Also of interest are polynucleotide molecules that encode at least 5 consecutive amino acids from a sequence selected from the group consisting of amino acids 1 to 21, amino acids 105 to 125, amino acids 137 to 203, amino acids 299 to 319 and amino acids 405 to 425 of SEQ ID NO:2.

A related aspect of the present invention provides isolated phospholipid transfer protein polypeptides comprising an amino acid sequence corresponding to a sequence of from 5 to 66 consecutive amino acids of SEQ ID NO:2. Preferred polypeptides include those comprising a sequence of amino acids within a region selected from the group consisting of amino acids 1 to 21, amino acids 105 to 125, amino acids 137 to 204, amino acids 299 to 319 and amino acids 405 to 425 of SEQ ID NO:2.

Another aspect of the present invention provides methods of preparing a mammalian phospholipid transfer protein or a polypeptide fragment thereof. The methods generally comprise culturing a cell into which has been introduced an expression vector comprising a DNA sequence encoding a mammalian phospholipid transfer protein or polypeptide fragment thereof, wherein said DNA sequence is operably linked to a transcriptional promoter and a transcriptional terminator, under conditions suitable for expression of said DNA sequence; and recovering the phospholipid transfer protein or polypeptide fragment thereof encoded by said DNA sequence. The expression vector may further comprise a secretory signal sequence operably linked to said DNA sequence. Preferred host cells include yeast cells and cultured mammalian cells.

The present invention further provides methods for detecting the presence of phospholipid transfer activity in a test sample. The methods comprise measuring the ability of a test sample to promote transfer of phospholipid between lipoproteins, such as from LDL to an acceptor lipoprotein, and comparing the transfer activity by the test sample to that obtained using recombinant phospholipid transfer protein. On the basis of this comparison, the presence of phospholipid transfer activity in the test sample is determined.

These and other aspects of the invention will become evident upon reference to the following detailed description of the invention.

DETAILED DESCRIPTION OF THE INVENTION

The present invention provides proteins that functionally mediate the transfer of phospholipid (PL). Phospholipid transfer protein (PLTP) transfers and exchanges phospholipids between lipoproteins.

The isolation and cloning of PLTP provides a valuable tool for investigating the process of phospholipid transport and the possible role of PLTP in cholesterol homeostasis and atherogenesis. PLTP is also valuable as a means to modulate the activity of CETP and thereby regulate lipid transfer activity and plasma levels of LDL and VLDL cholesterol.

The phospholipid transfer proteins of the present invention are preferably from mammals, especially primates including humans. Phospholipid transfer proteins will be understood to include proteins comprising the amino acid sequence of the representative human PLTP sequence shown in SEQ ID NO:2 from amino acid residue number 18 (Glu) to amino acid residue number 493 (Val). The proteins optionally include all or part of the amino-terminal sequence Met (amino acid number 1) to Ala (number 17) of SEQ ID NO:2. Phospholipid transfer proteins further include allelic and species variants of the illustrated sequences, as well as proteins that are engineered to contain minor sequence variations from naturally occurring PLTPs, including amino acid deletions and substitutions, particularly conservative substitutions, which do not significantly alter the essential properties of the protein. Of particular interest are those proteins that are substantially homologous to a naturally occurring PLTP, such as the representative human PLTP of SEQ ID NO:2. By "substantially homologous" is meant sequences that have at least about 85% homology, preferably at least 90%, and more preferably at least about 95% or more homology to the amino acid sequence of a naturally occurring PLTP and still retain the ability to transfer phospholipid. Essential properties for PLTP are the ability of the protein to transfer phospholipid from a donor lipoprotein to an acceptor lipoprotein. Donor lipoproteins include lipoproteins, such as LDL and VLDL, HDL and phospholipid vesicles, which may or may not include other lipids in the composition of the vesicle. Acceptor lipoproteins include lipoproteins such as LDL, VLDL and HDL. Of particular interest as an acceptor lipoprotein is HDL. Phospholipid transfer activity can be assayed as described in detail hereinafter.

Analysis of the cloned cDNA of SEQ ID NO:1 and the purified PLTP protein predicts a precursor PLTP protein that is proteolytically processed to an active 51 kDa species. Referring to SEQ ID NO:2, the protein contains six potential N-linked glycosylation sites (residues 64, 94, 117, 143, 245 and 398), four cysteine residues (residues 22, 146, 185 and 335) and five hydrophobic regions (residues 1–21, 105–125, 184–203, 299–319 and 405–425), which are believed to be important structural features. In particular, given the structural features of apolipoproteins and their lipid-binding domains, it is likely that these hydrophobic regions are important in the activity of the protein (see, e.g., Li et al., *J. Lipid Res.* 29:245–271, 1988).

In addition to the phospholipid transfer proteins described above, the invention includes PLTP polypeptides. PLTP polypeptides are fragments of the mature PLTP of at least 5 amino acids, generally less than about 100 amino acids, preferably less than about 67 amino acids in length. Of particular interest are polypeptides of from 12 to 20 amino acids. PLTP polypeptides may comprise a sequence of amino acids as shown in SEQ ID NO:2, or may be derived from a non-human PLTP or an allelic variant. The invention also includes engineered variant polypeptides that are substantially homologous to the corresponding sequence of a naturally occurring PLTP. PLTP polypeptides are useful, inter alia, as antigens for generating antibodies to PLTP. Particularly preferred fragments include fragments that interact with phospholipid molecules and promote the transfer of the phospholipid molecules from a donor lipoprotein, such as LDL, to an acceptor lipoprotein. Of particular interest are polypeptides from amino acid residue 163 (Lys) to amino acid residue 493 (Val) of SEQ ID NO:2 which the present inventors have demonstrated transfers phosphatidylcholine from LDL to HDL vesicles. Regions of homology between CETP and PLTP are of interest because both proteins are involved in lipid transport in the same metabolic pathways. Conserved regions for PLTP and CETP include, for example, amino acid residues 1 to 17, 210 to 230 and 262 to 293. Other regions of the PLTP molecule that are of interest include the hydrophobic regions disclosed above and regions that are conserved between proteins such as PLTP, CETP, phospholipase C, lipopolysaccharide binding protein and bactericidal permeability increasing protein.

The present invention further provides isolated polynucleotide molecules encoding phospholipid transfer proteins and phospholipid transfer polypeptides. Useful polynucleotide molecules in this regard include mRNA, genomic DNA, cDNA and synthetic DNA. For production of recombinant PLTP and PLTP polypeptides, cDNA is preferred. By "isolated" it is meant that the molecules are removed from their natural genetic milieu. Thus, the invention provides PLTP-encoding DNA molecules free of other genes with which they are ordinarily associated. In particular, the molecules are free of extraneous or unwanted coding sequences, and in a form suitable for use within genetically engineered protein production systems. A representative human PLTP cDNA is shown in SEQ ID NO:1. Those skilled in the art will recognize that equivalent sequences could be prepared by substituting alternative codons. The present invention includes these equivalent sequences, as well as additional sequences that specifically hybridize to naturally occurring or equivalent sequences. Such additional sequences whose complementary strand will hybridize to SEQ. ID NO:1 or its equivalent under conditions of high or moderate stringency, i.e. conditions that differentiate related molecules from background. Those skilled in the art will recognize that lower stringency conditions serve to identify sequences encoding functionally equivalent polypeptides having common structural features (e.g. allelic variants). For example, conditions of moderate stringency for probes of 100 nucleotides or greater include, prewashing in a solution of 5×SSC, 0.5% SDS, 1.0 mM EDTA (pH 8.0) and hybridization conditions of 50° C. in 5×SSC, overnight (Sambrook, et al., *Molecular Cloning: A Laboratory Manual,* 2nd ed., Cold Spring Harbor Laboratory Press, Cold Spring Harbor, N.Y., 1989, which is incorporated herein by reference). Conditions of higher stringency may be utilized by increasing temperature or decreasing the salt concentration of the hybridization solution. Determination of stringency hybridization conditions is within the level of ordinary skill in the art.

The present inventors have purified PLTP from human plasma. Analysis of the purified protein provided amino acid sequence information that was used to obtain a full-length cDNA encoding the protein. As disclosed in more detail hereinafter, PLTP was purified from pooled plasma obtained from normal individuals by ultracentrifugation. The fractionated plasma was separated by sequential chromatography with transfer activity assessed by the transfer of $^3$H-phosphatidycholine from phospholipid vesicles to HDL. The protein was concentrated by lyophilization, electrophoresed on a gradient gel and transferred onto a poly(vinylideme difluoride) membrane. A 51 kDa proteolytic fragment of PLTP was sequenced according to conventional chemical methods using an automated sequencer. These procedures allowed the purification of sufficient quantities of PLTP for determination of amino acid sequence data that could be used to design primers for cloning the cDNA.

As described in more detail in the following examples, the present inventors prepared degenerate oligonucleotide primers on the basis of amino acid sequence information obtained from a 51 kDa PLTP fragment. These primers were used in a polymerase chain reaction to generate a PLTP-encoding DNA fragment from a HepG2 cDNA library which allowed for the identification of a unique 25 bp DNA sequence. An antisense 25 bp oligonucleotide was radiolabeled and used as a probe to screen approximately $1.2 \times 10^6$ colonies from the HepG2 library immobilized on nylon membranes. The HepG2 library produced a partial clone that sequence analysis revealed was missing 5' sequence. A 1287 bp SstI fragment of the partial cDNA obtained from the HepG2 library was used to probe a northern blot (Rave et al. *Nucleic Acids Res.* 6:3559, 1979) revealing that the mRNA was present in a wide distribution of tissues, for example, placenta, pancreas, lung, kidney, liver, skeletal muscle and brain. Messenger RNA was also detected in microvascular, arterial and venous endothelial cells. The 1287 bp fragment was used to probe a cDNA library prepared from human umbilical vein endothelial cells (HUVE) of approximately $1.7 \times 10^6$ colonies immobilized on nylon membranes. Sequence analysis revealed a full length cDNA sequence of 1768 bp encoding PLTP.

As will be recognized by those skilled in the art, polynucleotide molecules encoding PLTP can be prepared using conventional cloning or synthesis techniques, or by using a combination of cloning and chemical synthesis. In general, the purified protein provides a tool for the preparation of cDNA and other polynucleotide molecules. Those skilled in the art will recognize that a variety of techniques could be applied to clone cDNA or genomic DNA molecules encoding PLTP in view of the instant disclosure. Suitable techniques are disclosed by, for example, Sambrook et al., *Molecular Cloning: A Laboratory Manual,* 2nd ed., Cold Spring Harbor Laboratory Press, Cold Spring Harbor, N.Y., 1989. DNA sequences may also be synthesized. Automated synthesis is preferred. For example, the entire coding sequence for PLTP can be chemically synthesized on the basis of the disclosed amino acid sequence. Methods for synthesizing oligonucleotides are known in the art. See, for example, Carruthers, U.S. Pat. No. 4,458,066 and Itakura, U.S. Pat. No. 4,356,270. The use of automated oligonucleotide synthesis equipment is preferred.

cDNA molecules encoding PLTP can be cloned from cDNA libraries constructed using mRNA from tissues or cells known to produce the protein. Various suitable methods for cloning PLTP DNA are known in the art, including hybridization of labeled oligonucleotide probes to libraries prepared from suitable cells, and the use of oligonucleotide primers to generate molecules using the polymerase chain reaction (Mullis et al., U.S. Pat. No. 4,683,195; Mullis, U.S. Pat. No. 4,683,202, which are incorporated herein by reference). Preferred sources of RNA for use in cDNA preparation include endothelial cells, liver and liver-derived cell lines, including hepatoma cell lines. A preferred hepatoma cell line is the HepG2 cell line (U.S. Pat. No. 4,393,133; ATCC No. HB 8065). Other species PLTP homologs may include, for example, rats, hamsters, mouse, primates other than human and rabbits. Methods for identification of species and tissues producing the protein are well known in the art.

PLTP can be conveniently produced in genetically engineered host cells according to conventional techniques.

Suitable host cells are those cell types that can be transformed or transfected with exogenous DNA and grown in culture, and include bacteria, fungal cells, and cultured higher eukaryotic cells. Techniques for manipulating cloned DNA molecules and introducing exogenous DNA into a variety of host cells are disclosed by Sambrook et al., ibid.

In general, a DNA sequence encoding PLTP is operably linked to a transcription promoter and terminator within an expression vector. The vector will commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct recombinant PLTP into the secretory pathway of the host cells, a secretory signal sequence (also known as a leader sequence, prepro sequence or pre sequence) is provided in the expression vector. The secretory signal sequence is joined to the DNA sequence encoding PLTP in the correct reading frame. Secretory signal sequences are commonly positioned 5' to the DNA sequence encoding the protein of interest, although certain signal sequences can be positioned 3' to the DNA sequence of interest (see, e.g., Welch et al., U.S. Pat. No. 5,037,743; Holland et al., U.S. Pat. No. 5,143,830). The secretory signal sequence may be that of the PLTP or another secreted protein, or it may be synthesized in accordance with known models (see, e.g., von Heijne, *Nuc. Acids Res.* 14: 4683–4690, 1986).

As noted above, higher eukaryotic cells, including cultured mammalian cells, may be used as hosts. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982) and DEAE-dextran mediated transfection (Ausubel et al., eds., *Current Protocols in Molecular Biology.*, John Wiley and Sons, Inc., N.Y., 1987), which are incorporated herein by reference. The production of recombinant proteins in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), BHK (ATCC No. CRL 1632), BHK 570 (ATCC No. CRL 10314) and 293 (ATCC No. CRL 1573; Graham et al., *J. Gen. Virol.* 36:59–72, 1977) cell lines. Additional suitable cell lines are known in the art and available from public depositories such as the American Type Culture Collection, Rockville, Md.

Other higher eukaryotic cells may also be used as hosts, including insect cells, plant cells and avian cells. Transformation of insect cells and production of foreign proteins therein is disclosed by Guarino et al., U.S. Pat. No. 5,162,222 and Bang et al., U.S. Pat. No. 4,775,624, which are incorporated herein by reference. The use of *Agrobacterium rhizogenes* directs transfer for expressing genes in plant cells has been reviewed by Sinkar et al., *J. Biosci. (Bangalore)* 11:47–58, 1987.

Yeast cells, particularly cells of the genus Saccharomyces, may also be used as host cells within the present invention. Methods for transforming yeast cells with exogenous DNA and producing recombinant proteins therefrom are disclosed by, for example, Beggs, *Nature* 275:104–109, 1978; MacKay, *Methods Enzymol.* 101:325–343, 1983; Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075, which are incorporated herein by reference. A preferred vector system for use in yeast is the POT1 vector system disclosed by Kawasaki et al. (U.S. Pat. No. 4,931,373), which allows transformed cells to be selected by growth in glucose-containing media. Transformation systems for other yeasts, including *Hansenula polymorpha, Schizosaccharomyces pombe, Kluyveromyces lactis, Kluyveromyces fragilis, Ustilago maydis, Pichia pastoris, Pichia guillermondii* and *Candida maltosa* are known in the art. See, for example, Gleeson et al., *J. Gen. Microbiol.* 132:3459–3465, 1986 and Cregg, U.S. Pat. No. 4,882,279.

Other fungal cells are also suitable as host cells. For example, Aspergillus cells may be utilized according to the methods of McKnight et al., U.S. Pat. No. 4,935,349, which is incorporated herein by reference. Methods for transforming *Acremonium chrysogenum* are disclosed by Sumino et al., U.S. Pat. No. 5,162,228, which is incorporated herein by reference.

Preferred prokaryotic host cells for use in carrying out the present invention are strains of the bacteria *Escherichia coli*, although Bacillus and other genera are also useful. Techniques for transforming these hosts and expressing foreign DNA sequences cloned therein are well known in the art (see, e.g., Sambrook et al., ibid.).

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. The growth conditions suitable for expression of a cloned DNA sequence will vary according to the particular host cells chosen. Selection of suitable conditions, including industrial-scale culture conditions, is within the level of ordinary skill in the art.

Those skilled in the art will recognize that the proteins and polypeptides of the present invention can also be produced in transgenic animals. Methods for generating transgenic animals and obtaining proteins therefrom have been previously described. See, for example, U.S. Pat. No. 4,873,191; U.S. Pat. No. 4,784,737; U.S. Pat. No. 4,873,316; European Patent Office publication EP 279,582 and PCT publication WO 92/11757.

Recombinant PLTP is purified from crude cell lysates or cell culture media using conventional techniques. Preferred procedures include antibody affinity adsorption chromatography; hydrophobic adsorbants using low pressure columns (e.g. Butyl-650 Toyopearl or the like) and HPLC columns; and ion exchange chromatography, both HPLC and low pressure.

According to the present invention, PLTP may be used to produce anti-hyperlipidemic agents in the treatment of primary and secondary hyperlipoproteinemias. The primary hyperlipoproteinemias are divided into two major classifications: those caused by an inherited single gene defect and those caused by a combination of multiple subtle genetic factors that act together with environmental insults. Familial lipoprotein lipase deficiency, familial type III hyperlipoproteinemia (dysbetalipoproteinemia), familial hypercholesterolemia, familial hypertriglyceridemia, and familial combined hyperlipidemia are monogenic hyperlipoproteinemias. Complex hypercholesterolemia and complex triglyceridemia are multifactorial forms of hyperlipoproteinemias. Secondary hyperlipoproteinemias are complications of a more generalized metabolic disturbance such as diabetes mellitus, hypothyroidism, or nephrotic syndrome.

In view of the difficulties of administering protein therapeutics, particularly in situations requiring chronic administration, it would be advantageous to develop small molecules, including small peptides and non-peptidic molecules, having anti-hyperlipidemic properties. Of particular interest are agents that produce a favorable lipoprotein profile (increased HDL/LDL ratio) and reduced total cholesterol levels. Compounds having these properties are useful in diminishing the clinical complications of atherosclerosis. PLTP provided by the present invention is a useful tool for identifying and developing such compounds.

To develop small peptide inhibitors of PLTP, overlapping synthetic peptides of about 25–40 amino acids are prepared according to the sequence of PLTP. of particular interest are the four hydrophobic stretches of the 81 kDa mature form of PLTP (residues 105–125, 184–203, 299–319 and 405–425 of SEQ ID NO:2). Peptides are assayed for the ability to inhibit PLTP by measuring the transfer of a labeled phospholipid, for example phosphatidylcholine, such as by direct measurement of transfer of radiolabeled substrate from LDL to $HDL_3$ or by a scintillation proximity assay. In the alternative, candidate molecules may be prepared by enzymatic digestion of PLTP or by expression of truncated DNA sequences in genetically engineered cells. Assay of these overlapping peptides reveals which region(s) of the molecule are responsible for promotion of the transfer activity. This information is used to design peptide inhibitors of PLTP. In general, peptide inhibitors will be from about 5–66 or more amino acids in length, up to the length of the entire mature protein, but will preferably be less than 20–25 amino acids in length.

PLTP inhibitor polypeptides are administered in an amount sufficient to reduce LDL and/or total cholesterol levels, and/or increase HDL levels. The pharmacokinetics and pharmacodynamics of these compounds can be established in experimental animal models (e.g. fat-fed rabbits). The average concentration of PLTP in normal human plasma is 1–3 µg/ml; therapeutic doses of PLTP inhibitors sufficient to produce a plasma concentration up to a similar level may be used.

For pharmaceutical use, PLTP inhibitors are formulated for parenteral (including subcutaneous, intramuscular, intravenous and mucosal) delivery according to conventional methods. In general, pharmaceutical formulations will include inhibitor molecules in combination with a pharmaceutically acceptable vehicle, such as saline, buffered saline, water or the like. Formulations may further include one or more excipients, preservatives, solubilizers, etc. One skilled in the art may formulate anti-hyperlipidemic molecules in an appropriate manner, such as those disclosed in *Remington's Pharmaceutical Sciences*, Gennaro, ed., Mack Publishing Co., Easton, Pa., 1990, which is incorporated herein by reference in its entirety.

PLTP can be used for detection of phospholipid transfer activity in an in vitro assay developed for the research environment. The research assay would, for example, be similar to the scintillation proximity assay (SPA) for CETP (Amersham, Arlington Heights, Ill.). Transfer of phospholipid between HDL and LDL or VLDL particles would be measured by monitoring the transfer of $^3$H-phosphatidylcholine (PC) from labeled donor (VLDL or LDL) to biotinylated and unlabeled (acceptor) HDL. The kit includes in separate containers an assay buffer; biotinylated acceptor substrate, for example, human HDL; a donor substrate, such as human LDL; recombinant PLTP and streptavidin SPA beads. Donor lipoproteins and $^3$H-PC are incubated with biotinylated acceptor lipoprotein in the presence of recombinant PLTP resulting in the transfer of label from donor to acceptor particle. The reaction would be terminated and measured by the addition of streptavidin SPA beads. The assay is performed in a microtiter plate (Dynatech, Chantilly, Va.) and is counted in a microtiter scintillation counter (Packard, Chicago, Ill.).

PLTP inhibition assays can also be used to screen non-peptidic compounds. Chemical libraries and microbiological fermentation broths are convenient sources of candidate compounds, although other sources, including plant and soil extracts, may also be readily tested. Briefly, the test sample is assayed for its ability to inhibit transfer of phospholipid from LDL to an acceptor lipoprotein. Results are compared to the PLTP standard. The use of recombinant PLTP as the standard is preferred. Lipoprotein acceptors include HDL, LDL, VLDL and chylomicrons. The phospholipid is labeled to provide a detectable signal. Detectable signals can include, but are not limited to, radiolabels, biotinylation and various chromophores. In one embodiment, the assay measures the transfer of radiolabeled phosphatidylcholine/LDL to $HDL_3$. The scintillation proximity assay may be adapted to high-throughput screening of potential inhibitors through the use of microtiter plates and a microplate scintillation counter. Results are compared to those obtained using purified (including recombinant) PLTP as a standard.

The primary structure of PLTP disclosed herein and the availability of large quantities of purified recombinant PLTP allow the elucidation of structural information that can be applied to modeling of PLTP and its interaction with phospholipids. A number of useful tools are available, including x-ray crystallography, NMR sequence alignment software, structure prediction programs and threading algorithms (inverse protein folding). Data generated using these methods are then used to determine three-dimensional structure. Structural information is then applied to the design and/or identification of candidate phospholipid transfer protein inhibitors.

The invention is illustrated by the following non-limiting examples.

EXAMPLE I

Purification of PLTP

HDL was isolated by conventional methods from 2 liters of citrated plasma by ultracentrifugation (d 1.063–1.21 g/ml) at 40,000 rpm for 72 hours in a 50.2 rotor (Smith Kline Beckman, Fullerton, Calif.) as disclosed in *Methods Enzymol.* 128:155–158, 227–228, 1986, which is incorporated herein by reference. The clear 1.21 g/ml "middle" fraction was isolated and assayed for transfer activity.

The transfer activity assay was assessed using $^3$H-phosphatidylcholine by measuring the transfer of the radiolabeled phospholipid from HDL to LDL. HDL, the lipoprotein donor was labeled by the direct addition of $_3$H-phosphatidylcholine (NEN-Dupont, Boston, Mass.) dissolved in 95% ethanol to the isolated HDL fraction (described above) and stirred gently (as disclosed in Tollefson et al. ibid.). The transfer of labeled phospholipid was measured in the following reaction: $HDL_3$ (d=1.125–1.21 g/ml) lipoprotein donor, with incorporated $^3$H-phosphatidylcholine ($^3$H-PC), was incubated with LDL (d=1.063–1.019) lipoprotein acceptor and test sample in the presence or absence of a source of lipid transfer activity. The assay mixture was incubated for three hours in a circulating 37° C. water bath. Transfer activity was then arrested by transferring the mixture to an ice bath. Donor and acceptor lipoproteins were separated by adding dextran sulfate (0.1% w/v) and $MgCl_2$ (50 ppm) to the assay mixture to precipitate LDL. An aliquot of the supernatant was counted in a Packard scintillation counter. Transfer activity was expressed as the percentage of labeled substrate ($^3$H-PC) transferred from $HDL_3$ to LDL relative to a control incubation lacking lipid transfer activity. Within the assay, the optimal lipoprotein donor:acceptor ratio was normally a 1:5 mass ratio, and the percentage of substrate transferred was optimized to approximately 30% (just within the linear range of lipid transfer in the assay).

The transfer of phosphatidylcholine from liposomes to HDL was made using an assay that monitored the transfer of radiolabeled PC (Damen et al. *Biochimica et Biophysica Acta* 712:444–453, 1982). Liposomes were prepared consisting of phosphatidylcholine/phosphatidylserine/cholesterol with a molar ratio of 4:1:5. Aliquots of five to ten micromolar $^3$H-PC (NEN-Dupont) were added to the mixture of PC, PS and cholesterol and dried thoroughly under high vacuum after evaporation of the organic solvent under a stream of nitrogen. One milliliter of 150 mM NaCl and 10 mM Tris buffer was added and the lipid was dispersed by pulsed sonication. The resulting lipid was 95% pure unilamellar liposome as analyzed by Sepharose CL-4B chromatography. HDL was isolated by sequential centrifugation of human plasma as described above. Purification fractions were tested for phospholipid transfer activity by incubation with $^3$H-PC liposomes and HDL. The liposomes (125 nmol $^3$H-PC) and HDL (250 μg protein) were incubated with 1–300 μl of the fraction to be assayed in stoppered polypropylene micro test tubes in final volume of 400 μl of buffer containing 150 mM NaCl and 10 mM Tris (pH 7.4). The reaction was stopped by the addition of 300 μl of a buffer with the final concentration of 320 mM NaCl, 92 mM $MnCl_2$ and 200 units of heparin/ml. The mixture was vortexed vigorously and incubated at room temperature for 10 minutes. After incubation the mixture was placed in an microcentrifuge for 10 minutes at 12,000 rpm. The resulting clear supernatant was analyzed for percent radioactivity relative to control without activity fraction added.

Purification of the fraction that contained the phospholipid transfer activity was done using sequential chromatography beginning with separation on a column of beaded agarose matrix (PHENYL-SEPHAROSE, Pharmacia, Piscataway, N.J.) (200 mls in a 2.5×50 cm column). The column was equilibrated in 2.0M NaCl and 10 mM Tris (pH 7.4). Approximately 700–800 mls of the middle active fraction was applied to the column and washed with 200 mls of the equilibration buffer at a flow rate of 100 mls/hr. The column was washed overnight at 4° C. with 1800 mls of 10 mM Tris and 0.15M NaCl (pH 7.4). Eighteen milliliters fractions were eluted with 250 mls of water and 10 μl of 25 mg/ml aprotinin were added to fraction 8–30 after collection. The fractions were assayed for phospholipid transfer.

The active fractions were pooled from the PHENYL-SEPHAROSE column elution and applied to a heparin sepharose column (40 mls in a 2.5×10 cm column). The column of HEPARIN-SEPHAROSE (Pharmacia) was first equilibrated in buffer containing 50 mM NaCl, 10 mM Tris and 1 mM EDTA (pH 7.4). The pooled fractions of approximately 300–400 mls were adjusted to a final concentration of the equilibration buffer by adding 0.29 g NaCl, 1 ml of 1.0M Tris (pH 7.4) and 1 ml of 1.0M EDTA (pH 7.4) per 100 ml of phenyl sepharose eluent and mixed for 30 minutes. The fibrin was removed by centrifugation at 4° C. and 3000 rpm for 30 minutes. The liquid phase was applied to the heparin sepharose column at 50 mls/hr followed by washing in the equilibration buffer overnight at a rate of 20 mls/hr. Eluent was collected using 150 mls of buffer containing 0.5M NaCl, 10 mM Tris and 1 mM EDTA (pH 7.4) in 7.0 ml fractions. The collected fractions were assayed for phospholipid transfer activity as described previously.

The active fractions were pooled and passed over a Q FAST FLOW SEPHAROSE column (Pharmacia) (50 mls in a 2.5×10 cm column). The QFF column was equilibrated using a buffer containing 25 mM Tris and 1 mM EDTA (pH 7.4) with a flow rate of 200 mls/hr. The pooled fractions from the heparin sepharose column purification were dialyzed against the QFF equilibration buffer. The dialyzed solution was applied to the QFF column and washed with 50 mls of equilibration buffer. Elution was done using 50 mls of equilibration buffer followed by 50 mls of equilibration buffer containing 1.0M NaCl. The collected fractions were assayed for phospholipid transfer activity as described previously.

After pooling the active fractions, they were further purified using a Butyl-650 Toyopearl (BTP) column (200 mls in 0.9×60 cm column) with a flow rate of 200 mls/hr. The column was equilibrated with a buffer containing 2.0M NaCl, 10 mM Tris and 1 mM EDTA (pH 7.4). The pooled fractions were brought to a final concentration of 2.0M NaCl by adding 88 mg of NaCl to each ml of pool and applied to the BTP column. The column was washed with 50 mls of equilibration buffer followed by 100 mls of a wash buffer containing 1.0M NaCl, 10 mM Tris and 1 mM EDTA (pH 7.4) in 100 mls water. Fractions of 8.0 mls each were collected using the following sequential elution buffers: 100 mls of 0.5M Tris and 1 mM EDTA (pH 7.4), 100 mls of 50 mM Tris and 1 mM EDTA (pH 7.4), 100 mls of 3.0 mM Tris and 1 mM EDTA (pH 7.4) and finally 100 mls of water. The fractions containing 0.5 Tris were dialyzed against the first elution buffer and all the fractions were assayed for phospholipid transfer activity as described previously.

A final separation was made using a HW-55 Toyopearl column (200 mls in 0.9×60 cm column). The column was equilibrated using a buffer containing 10 mM Tris and 0.15N NaCl (pH 7.4). Approximately 5 mls of the 3 mM Tris pooled active fractions from the BTP column was applied to the HW-55 column. The eluent was collected as 6 ml fractions and assayed for phospholipid transfer as described previously.

The active fractions were pooled and concentrated by lyophilization. The concentrated fraction was analyzed by electrophoresis on a 10–20% gradient SDS-PAGE (Daiichi Pure Chemicals Co., Ltd., Tokyo, Japan) and electroblotted onto poly(vinylideme difluoride) membrane (Applied Biosystems, Inc., Foster City, Calif.). SDS gels were quick stained in a solution of 0.2% Coomassie Brilliant Blue R by weight, 10% acetic acid, 25% methanol and briefly destained in the same solution without the dye. A single major band of 51 kDa was seen, cut out and electroeluted. Subsequent fractions yielded a mixture of the PLTP revealing an 81 kDa band and the 51 kDA band, which was determined to be a proteolytic fragment of the mature 81 kDa protein.

PLTP antisera was prepared by immunizing a single New Zealand White rabbit with PLTP (50 µg 51 k Da fragment purified from human plasma and electroeluted from SDS gels, as described above. Peroxidase-conjugated goat anti-rabbit IgG heavy and light chain were used as secondary antibodies. Western analysis was done using a 12% gradient SDS PAGE gels. Proteins were electrotransferred to nitrocellulose membranes (Schleicher & Schuell, Keene, N.H.) overnight at 110 mA constant current using Transblot buffer (25 mM Tris, pH 8.3, 19 mM glycine, 20% methanol). Nitrocellulose membranes were blocked in 5% milk, then stained with the double antibody method using horseradish peroxidase-conjugated second antibody. Western blotting detection reagents were used to visualize PLTP protein. The antisera preparation specifically recognized the 51 kDa and 81 kDa forms of PLTP.

Concentrated PLTP was reisolated by electrophoresis on 10–20% gradient SDS-PAGE (Daiichi Pure Chemicals Co., Ltd., Tokyo, Japan) and electroblotted onto poly(vinylideme difluoride) membrane (Applied Biosystems, Inc., Foster City, Calif.). The 81 kDa mature protein and 51 kDa fragment were excised, and their N-terminal amino acid sequences determined with an Applied Biosystems Model 470A sequencer using the manufacturer's programming and chemicals. Internal peptides from the 51 kDa fragment were generated by trypsin digestion of PLTP on PVDF. A sequence analysis resulted in a 21-amino acid $NH_2$-terminal sequence for the 51 kDa fragment (residues 163–184 of SEQ ID NO:2) and a 10-amino acid $NH_2$-terminal sequence for the 81 kDa protein (residues 18–28 of SEQ ID NO:2). Purified preparations of an 81 kDa and 51 kDa PLTP proteins were found to promote the transfer of $^3$H-radiolabeled PC in the PLTP assay described previously.

EXAMPLE II

PCR Amplification of DNA Encoding PLTP

Degenerate primers were designed based on the 21-amino acid $NH_2$-terminal sequence of the 51 kDa fragment of PLTP. All oligonucleotides were synthesized on an Applied Biosystems 380A DNA synthesizer. Polymerase chain reaction using degenerate Oligonucleotides ZC6086 (SEQ. ID NO:3) and ZC6087 (SEQ. ID NO:4) generated a PCR product from a Hep G2 cDNA library that resulted in the identification of an unique 25 bp sequence for PLTP.

The cDNA library was prepared from Hep G2 cells essentially as described by Houamed et al. (*Science* 252: 1318–1321, 1991, and is incorporated herein by reference) using the vector Zem 228CC. This vector was prepared from plasmid Zem228, a pUC18-based expression vector containing a unique Bam HI site for insertion of cloned DNA between the mouse metallothionein-1 promoter and SV40 transcription terminator and an expression unit containing the SV40 early promoter, neomycin resistance gene, and SV40 terminator. Plasmid Zem228 was modified to delete the two Eco RI sites by partial digestion with Eco RI, blunting with DNA polymerase I (Klenow fragment) in the presence of dNTPs, and re-ligation. Digestion of the resulting plasmid with Bam HI followed by ligation of the linearized plasmid with Bam HI-Eco RI adapters resulted in a unique Eco RI cloning site. The resultant plasmid was designated Zem228R. The Sst I site between the SV40 promoter and the mouse metallothionein-1 promoter was destroyed by linearizing Zem228R with Sst I, blunting the adhesive ends with T4 DNA polymerase in the presence of dNTPs and religating the linearized, blunt-ended fragment. A plasmid in which the Sst I site was destroyed was designated Zem228Ra.

In order to facilitate directional insertion of cDNA fragments into Zem288Ra, an adapter was synthesized which contained a 5' Eco RI adhesive end, an internal Sst I site and a 3'Eco RI adhesive end that does not regenerate an Eco RI site upon ligation with an Eco RI adhesive end. Plasmid Zem228Ra was linearized by digestion with Eco RI, and the linearized plasmid was treated with calf alkaline phosphatase to prevent recircularization. The linearized plasmid was ligated with kinased oligonucleotides ZC3169 and ZC3168 (SEQ. ID NO:5 and NO:6, respectively). A plasmid containing inserted adapter was designated Zem228C.

To improve the ability achieve an Eco RI+Sst I cleavage of the Zem228C vector, an oligonucleotide adapter was synthesized that contained an internal Eco RI site flanked by Eco RI adhesive ends that do not regenerate Eco RI sites upon ligation with Eco RI adhesive ends. Oligonucleotides ZC1773 and ZC1774 (SEQ. ID NO:7 and NO:8 respectively) were kinased and annealed to form the adapter. Plasmid Zem228C was linearized by digestion with Eco RI, and the linearized vector and kinased adapter were ligated. A plasmid containing the adapter was confirmed and sequenced. Sequence analysis revealed that the plasmid contained a 30 bp DNA insert between the new Eco RI site and the downstream Sst I site. Since an Eco RI+Sst I cleavage of the vector prior to the insertion of a cDNA sequence removes the additional DNA sequence, the inserted DNA was not removed. The plasmid was designated Zem1698 (also known as Zem228CC).

The 21-amino acid sequence of the 51 kDa fragment of PLTP was used to design degenerate oligonucleotides ZC6086 (SEQ. ID NO:3) and ZC6087 (SEQ. ID NO:4). The HepG2 cDNA library was used as a template for amplification using a polymerase chain reaction. The polymerase chain reaction was done using the reagents and recommended protocol for HOT START PCR (Perkin-Elmer Cetus). A wax pellet was used in a 100 µl reaction with 1 µg of template DNA. A Perkin-Elmer Cetus DNA thermal cycler was utilized for 40 cycles of amplification using a step program (95° C., 1 minute; 45° C., 1 minute; 72° C., 1 minute) followed by a 10 minute final extension at 72° C.

The amplification resulted in the generation of an 81-bp product, which was excised by digestion with EcoRI and BamHI restriction enzymes. The excised 73 bp fragment was purified from a 4% NuSieve gel (FMC Bioproducts, Rockland, Me.) with NA-45 paper (Schleicher and Schuell, Keene, N.H.), and directly cloned into the vector pUC18. Plasmids were transformed into *E. coli* DH 10B cells (GIBCO BRL, Gaithersburg, Md.). After transformation, colonies were screened and selected by blue/white screening and by colony PCR (by adding cells from single colonies of DH 10B *E. coli* cells containing the 73 bp PLTP PCR product to a standard PCR reaction) with degenerate primers ZC6086 (SEQ. ID NO:3) and ZC6087 (SEQ. ID NO:4). The 73-bp insert cloned into pUC18 was sequenced by the dideoxy chain termination method using [$\alpha$-$^{35}$S] dATP (DuPont/New England Nuclear, Boston, Mass.). Sequence analysis of the 73 bp fragment, provided a unique 25-bp DNA sequence.

An antisense oligonucleotide probe was designed from the 25-bp sequence (ZC6203; SEQ ID NO:9) was end-labeled with $\alpha$-$^{32}$P-dATP using T-4-polynucleotide kinase and used to probe the HepG2 cDNA library.

An aliquot of purified plasmid DNA from the HepG2 cDNA library was titered, and *E. coli* DH10B cells were transformed with an appropriate amount of DNA to obtain 60,000 colonies per large LB-Amp (100 µg/ml) agar plate (150×15 mm tissue culture dish, twenty dishes total or approximately 1.2×10$^6$ colonies). Plates were grown overnight until colonies were easily visible. Nylon membranes (Biotrans Nylon membranes; ICN Biomedicals) were placed on the agar plates for 5 minutes; placed on filter paper soaked with 0.5M NaOH, 1.5M NaCl for 15 minutes; then neutralized on filter paper soaked with 0.5M Tris; 1.5M NaCl pH 8 for 15 minutes. Nylon filters were air dried, then baked at 80° C. in a vacuum oven for 1 hour. Filters were then prewashed with 3×SSC, 0.1% SDS for 1 hour at 65° C. and prehybridized in Ulrichs buffer containing 20% formamide (50 ml Denhardt's solution [3×SSC, Ficoll, polyvinylpyrollidone and BSA, each to a concentration of 0.02% w/v], 250 ml formamide, 5 ml sonicated, boiled salmon sperm DNA [10 mg/ml], 25 mg ATP, 20 ml 1.25M sodium phosphate pH 7.0, 5 ml 0.1M sodium pyrophosphate, 125 ml 20×SSC, 45 ml H$_2$O) overnight at 37° C. The filters were then placed in fresh Ulrich's buffer containing 5×10$^7$ cpm of boiled probe (described above) per ml overnight at 37° C. Filters were then washed two times, ten minutes per wash, in 2×SSC, 0.1% SDS at 50° for 15 minutes, 55° C. for 15 minutes and finally for 30 minutes at 60° C. in tetramethylammonium chloride (TMAC). Filters were blotted partially dry on Whatman filter paper, wrapped in Saran Wrap, and exposed to film for 1–3 days at −70° C. One positive clone was selected and recovered with a sterile toothpick and applied to an LB amp plate. Minipreps were generated and corresponding insert sizes determined by restriction digestion with Bam HI and size determination on a 1% agarose gel. Insert size was approximately 1500 bp and found to be incomplete at the 5' end when sequence analysis was performed.

The partial HepG2 DNA fragment was digested with SstI and a 1287 bp fragment was generated. The 20 ng of the 1287 bp fragment was radiolabeled with $\alpha$-$^{32}$PdNTPs, according to the manufacturer's specifications using a Megaprime kit (Amersham). A multiple tissue northern blot (Clontech, Palo Alto, Calif.) was probed and revealed that the transcript was present in many tissues, including, placenta, pancreas, lung, liver, skeletal muscle and brain. PCR analysis also revealed the presence of the PLTP cDNA in a human umbilical endothelial vein cDNA library.

The HUVE cDNA library was prepared from human umbilical vein endothelial (HUVE) cells (Cell Systems, Kirkland, Wash.) as described previously. A probe was prepared as described for the northern blot from the 1287 bp SstI DNA fragment and used to screen 1.7×10$^6$ colonies from the HUVE cDNA library, essentially as described for the HepG2 cDNA library screening with the exception that the hybridization solution contained 50% formamide and the washes were done twice in 2×SSC, 0.1% SDS at 60° C. for 15 minutes each. Eighteen clones were identified as positive and verified using a polymerase chain reaction screening using nested primers based on the DNA sequence of the 1500 bp partial cDNA clone. Plasmid DNA was digested with SstI and EcoRI and compared to the partial cDNA from the HepG2 library for verification of a full length cDNA.

Analysis of the translated cDNA revealed that the 51 kDa protein originally purified was the result of proteolytic cleavage of a mature 81 kDa PLTP protein. Western blot analysis demonstrated that antiserum to PLTP specifically recognized both the mature form (81 kDa) of PLTP and the 51 kDa fragment.

Referring to SEQ. ID NO:1, the mature cDNA encodes a putative leader of 17 amino acids (positions 1–17) with a 8/9 match in the Kozak sequence flanking the initiator codon (Kozak, *Nuc. Acids Res.* 12:857–872, 1984). The open reading frame contains 1518 bp followed by 202 bp in the 3' untranslated region. The presumed primary translation product is preceded by an open reading frame at the 5'end. The calculated molecular weight based upon the primary sequence for the active 81 kDa form of PLTP is 54,719 Da for the apparent entire coding region. The difference in the calculated and observed molecular weights may be due to N- and O-linked glycosylation and acylation, which are common for apoproteins. Six potential N-glycosylation sites are present, predicted from sequence located at amino acid positions 64, 94, 117, 143, 245 and 398. There are seven potential protein kinase C phosphorylation sites found at amino acid residues 27, 124, 160, 242, 336, 374 and 430. Four cysteines are found in the mature PLTP protein at amino acid residues 22, 146, 185 and 335. Five extended putative hydrophobic regions are found at amino acid residues 1–21, 105,–125, 184–203, 299–319, and 405–425.

PLTP cDNA inserted into Zem228cc as a ~1800 bp SstI-EcoRI insert, designated PLTP14 has been deposited with American Type Culture Collection, 12301 Parklawn Dr., Rockville, Md., as an *E. coli* DH10-B transformant with the accession number 69509.

Although certain embodiments of the invention have been described in detail for purposes of illustration, it will be readily apparent to those skilled in the art that various modifications may be made without departing from the spirit and scope of the invention. Accordingly, the invention is not limited except as by the appended claims.

---

We claim:

1. A method for detecting the presence of a phospholipid transfer activity in a test sample comprising:

providing a sample of recombinant phospholipid transfer protein (PLTP) selected from the group consisting of (a) a polypeptide having the amino acid sequence of SEQ ID NO:2 from amino acid residue number 1 (Met) to amino acid residue number 493 (Val); (b) a polypeptide having the amino acid sequence of SEQ ID NO:2 from amino acid residue number 18 (Glu) to amino acid residue number 493 (Val); (c) a polypeptide having the amino acid sequence of SEQ ID NO:2 from amino acid residue number 137 (Gly) to amino acid residue number 493 (Val); and (d) allelic variants of a, b, and c;

measuring the ability of a test sample to inhibit transfer of phospholipid from LDL to an acceptor lipoprotein; and comparing the inhibition by the test sample to that obtained using recombinant phospholipid transfer protein, and determining from said comparison the presence of a phospholipid transfer activity in the test sample.

2. A kit for detection of phospholipid transfer activity comprising:

a first container containing radiolabeled phosphatidylcholine-LDL;

a second container containing an acceptor lipoprotein;

a third container containing a donor lipoprotein; and a fourth container containing a phospholipid transfer protein selected from the group consisting of (a) a polypeptide having the amino acid sequence of SEQ ID NO:2 from amino acid residue number 1 (Met) to amino acid residue number 493 (Val); (b) a polypeptide having the amino acid sequence of SEQ ID NO:2 from amino acid residue number 18 (Glu) to amino acid residue number 493 (Val); (c) a polypeptide having the amino acid sequence of SEQ ID NO:2 from amino acid residue number 137 (Gly) to amino acid residue number 493 (Val); and (d) allelic variants of a, b, and c.

3. A kit according to claim 2 wherein said kit further comprises a fifth container containing an agent that facilitates the separation of labeled acceptor lipoprotein from unlabeled acceptor lipoprotein.

4. A kit according to claim 2 wherein the acceptor lipoprotein is HDL.

\* \* \* \* \*

UNITED STATES PATENT AND TRADEMARK OFFICE
CERTIFICATE OF CORRECTION

PATENT NO. : 5,610,019
DATED : March 11, 1997
INVENTOR(S) : Joseph R. Day et al.

It is certified that error appears in the above-identified patent and that said Letters Patent is hereby corrected as shown below:

Title page,
Item [73], Assignee, please add the following:
-- University of Washington, Seattle, Washington --

Signed and Sealed this

Seventh Day of December, 2004

JON W. DUDAS
*Director of the United States Patent and Trademark Office*

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 1750 base pairs
        ( B ) TYPE: nucleic acid -continued

```
       ( C ) STRANDEDNESS: double
       ( D ) TOPOLOGY: linear ( i i ) MOLECULE TYPE: cDNA ( v i i ) IMMEDIATE SOURCE:
           ( B ) CLONE: PLTP ( i x ) FEATURE:
           ( A ) NAME/KEY: CDS
           ( B ) LOCATION: 88..1560

( x i ) SEQUENCE DESCRIPTION: SEQ ID NO:1:
```

| | | | | | | |
|---|---|---|---|---|---|---|
| GTGGCCGCCG | TCGCCCGGAT | CCCCTGAGCT | GCCCGCCATC | CCACGTGACC | GCGCCGCCCC | 60 |
| CCAGCTCCAC | CGCTGAGCCC | GCTCGCC ATG GCC CTC TTC GGG GCC CTC TTC | | | | 111 |
| | | Met Ala Leu Phe Gly Ala Leu Phe | | | | |
| | | 1                       5 | | | | |

```
CTA GCG CTG CTG GCA GGC GCA CAT GCA GAG TTC CCA GGC TGC AAG ATC    159
Leu Ala Leu Leu Ala Gly Ala His Ala Glu Phe Pro Gly Cys Lys Ile
    10              15                  20

CGC GTC ACC TCC AAG GCG CTG GAG CTG GTG AAG CAG GAG GGG CTG CGC    207
Arg Val Thr Ser Lys Ala Leu Glu Leu Val Lys Gln Glu Gly Leu Arg
25              30                  35                  40

TTT CTG GAG CAA GAG CTG GAG ACT ATC ACC ATT CCG GAC CTG CGG GGC    255
Phe Leu Glu Gln Glu Leu Glu Thr Ile Thr Ile Pro Asp Leu Arg Gly
                45                  50                  55

AAA GAA GGC CAC TTC TAC TAC AAC ATC TCT GAG GTG AAG GTC ACA GAG    303
Lys Glu Gly His Phe Tyr Tyr Asn Ile Ser Glu Val Lys Val Thr Glu
                60                  65                  70

CTG CAA CTG ACA TCT TCC GAG CTC GAT TTC CAG CCA CAG CAG GAG CTG    351
Leu Gln Leu Thr Ser Ser Glu Leu Asp Phe Gln Pro Gln Gln Glu Leu
        75                  80                  85

ATG CTT CAA ATC ACC AAT GCC TCC TTG GGG CTG CGC TTC CGG AGA CAG    399
Met Leu Gln Ile Thr Asn Ala Ser Leu Gly Leu Arg Phe Arg Arg Gln
    90                  95                  100

CTG CTC TAC TGG TTC TTC TAT GAT GGG GGC TAC ATC AAC GCC TCA GCT    447
Leu Leu Tyr Trp Phe Phe Tyr Asp Gly Gly Tyr Ile Asn Ala Ser Ala
105                 110                 115                 120

GAG GGT GTG TCC ATC CGC ACT GGT CTG GAG CTC TCC CGG GAT CCC GCT    495
Glu Gly Val Ser Ile Arg Thr Gly Leu Glu Leu Ser Arg Asp Pro Ala
                125                 130                 135

GGA CGG ATG AAA GTG TCC AAT GTC TCC TGC CAG GCC TCT GTC TCC AGA    543
Gly Arg Met Lys Val Ser Asn Val Ser Cys Gln Ala Ser Val Ser Arg
            140                 145                 150

ATG CAC GCG GCC TTC GGG GGA ACC TTC AAG AAG GTG TAT GAT TTT CTC    591
Met His Ala Ala Phe Gly Gly Thr Phe Lys Lys Val Tyr Asp Phe Leu
        155                 160                 165

TCC ACG TTC ATC ACC TCA GGG ATG CGC TTC CTC CTC AAC CAG CAG ATC    639
Ser Thr Phe Ile Thr Ser Gly Met Arg Phe Leu Leu Asn Gln Gln Ile
170                 175                 180

TGC CCT GTC CTC TAC CAC GCA GGG ACG GTC CTG CTC AAC TCC CTC CTG    687
Cys Pro Val Leu Tyr His Ala Gly Thr Val Leu Leu Asn Ser Leu Leu
185                 190                 195                 200

GAC ACC GTG CCT GTG CGC AGT TCT GTG GAC GAG CTT GTT GGC ATT GAC    735
Asp Thr Val Pro Val Arg Ser Ser Val Asp Glu Leu Val Gly Ile Asp
                205                 210                 215

TAT TCC CTC ATG AAG GAT CCT GTG GCT TCC ACC AGC AAC CTG GAC ATG    783
Tyr Ser Leu Met Lys Asp Pro Val Ala Ser Thr Ser Asn Leu Asp Met
            220                 225                 230

GAC TTC CGG GGG GCC TTC TTC CCC CTG ACT GAG AGG AAC TGG AGC CTC    831
Asp Phe Arg Gly Ala Phe Phe Pro Leu Thr Glu Arg Asn Trp Ser Leu
        235                 240                 245
```

| | | | | | | | | | | | | | | | | |
|---|---|---|---|---|---|---|---|---|---|---|---|---|---|---|---|---|
| CCC | AAC | CGG | GCA | GTG | GAG | CCC | CAG | CTG | CAG | GAG | GAA | GAG | CGG | ATG | GTG | 879 |
| Pro | Asn 250 | Arg | Ala | Val | Glu | Pro 255 | Gln | Leu | Gln | Glu | Glu 260 | Glu | Arg | Met | Val | |
| TAT | GTG | GCC | TTC | TCT | GAG | TTC | TTC | TTC | GAC | TCT | GCC | ATG | GAG | AGC | TAC | 927 |
| Tyr 265 | Val | Ala | Phe | Ser | Glu 270 | Phe | Phe | Phe | Asp | Ser 275 | Ala | Met | Glu | Ser | Tyr 280 | |
| TTC | CGG | GCG | GGG | GCC | CTG | CAG | CTG | TTG | CTG | GTG | GGG | GAC | AAG | GTG | CCC | 975 |
| Phe | Arg | Ala | Gly | Ala 285 | Leu | Gln | Leu | Leu | Leu 290 | Val | Gly | Asp | Lys | Val 295 | Pro | |
| CAC | GAC | CTG | GAC | ATG | CTG | CTG | AGG | GCC | ACC | TAC | TTT | GGG | AGC | ATT | GTC | 1023 |
| His | Asp | Leu | Asp 300 | Met | Leu | Leu | Arg | Ala 305 | Thr | Tyr | Phe | Gly | Ser 310 | Ile | Val | |
| CTG | CTG | AGC | CCA | GCA | GTG | ATT | GAC | TCC | CCA | TTG | AAG | CTG | GAG | CTG | CGG | 1071 |
| Leu | Leu | Ser 315 | Pro | Ala | Val | Ile | Asp 320 | Ser | Pro | Leu | Lys | Leu 325 | Glu | Leu | Arg | |
| GTC | CTG | GCC | CCA | CCG | CGC | TGC | ACC | ATC | AAG | CCC | TCT | GGC | ACC | ACC | ATC | 1119 |
| Val | Leu | Ala 330 | Pro | Pro | Arg | Cys | Thr 335 | Ile | Lys | Pro | Ser | Gly 340 | Thr | Thr | Ile | |
| TCT | GTC | ACT | GCT | AGC | GTC | ACC | ATT | GCC | CTG | GTC | CCA | CCA | GAC | CAG | CCT | 1167 |
| Ser 345 | Val | Thr | Ala | Ser | Val 350 | Thr | Ile | Ala | Leu | Val 355 | Pro | Pro | Asp | Gln | Pro 360 | |
| GAG | GTC | CAG | CTG | TCC | AGC | ATG | ACT | ATG | GAC | GCC | CGT | CTC | AGC | GCC | AAG | 1215 |
| Glu | Val | Gln | Leu | Ser 365 | Ser | Met | Thr | Met | Asp 370 | Ala | Arg | Leu | Ser | Ala 375 | Lys | |
| ATG | GCT | CTC | CGG | GGG | AAG | GCC | CTG | CGC | ACG | CAG | CTG | GAC | CTG | CGC | AGG | 1263 |
| Met | Ala | Leu | Arg 380 | Gly | Lys | Ala | Leu | Arg 385 | Thr | Gln | Leu | Asp | Leu 390 | Arg | Arg | |
| TTC | CGA | ATC | TAT | TCC | AAC | CAT | TCT | GCA | CTG | GAG | TCG | CTG | GCT | CTG | ATC | 1311 |
| Phe | Arg | Ile 395 | Tyr | Ser | Asn | His | Ser 400 | Ala | Leu | Glu | Ser | Leu 405 | Ala | Leu | Ile | |
| CCA | TTA | CAG | GCC | CCT | CTG | AAG | ACC | ATG | CTG | CAG | ATT | GGG | GTG | ATG | CCC | 1359 |
| Pro | Leu 410 | Gln | Ala | Pro | Leu | Lys 415 | Thr | Met | Leu | Gln | Ile 420 | Gly | Val | Met | Pro | |
| ATG | CTC | AAT | GAG | CGG | ACC | TGG | CGT | GGG | GTG | CAG | ATC | CCA | CTA | CCT | GAG | 1407 |
| Met 425 | Leu | Asn | Glu | Arg | Thr 430 | Trp | Arg | Gly | Val | Gln 435 | Ile | Pro | Leu | Pro | Glu 440 | |
| GGC | ATC | AAC | TTT | GTG | CAT | GAG | GTG | GTG | ACG | AAC | CAT | GCG | GGA | TTC | CTC | 1455 |
| Gly | Ile | Asn | Phe | Val 445 | His | Glu | Val | Val | Thr 450 | Asn | His | Ala | Gly | Phe 455 | Leu | |
| ACC | ATC | GGG | GCT | GAT | CTC | CAC | TTT | GCC | AAA | GGG | CTG | CGA | GAG | GTG | ATT | 1503 |
| Thr | Ile | Gly | Ala 460 | Asp | Leu | His | Phe | Ala 465 | Lys | Gly | Leu | Arg | Glu 470 | Val | Ile | |
| GAG | AAG | AAC | CGG | CCT | GCT | GAT | GTC | AGG | GCG | TCC | ACT | GCC | CCC | ACA | CCG | 1551 |
| Glu | Lys | Asn 475 | Arg | Pro | Ala | Asp | Val 480 | Arg | Ala | Ser | Thr | Ala 485 | Pro | Thr | Pro | |
| TCC | ACA | GCA | GCTGTCTGAG | CCCTCAATCC | CCAAGCTGGC | AGCTGTCATT | | | | | | | | | | 1600 |
| Ser | Thr | Ala 490 | | | | | | | | | | | | | | |

CAGGACCCCA ACCCCTCTCA GCCCCTCTTT TCCCACATTC ATAGCCTGTA GTGCCCCCTC    1660

TAACCCCCAG TGCCACAGAG AAGACGGGAT TTGAAGCTGT ACCCAATTTA ATTCCATAAT    1720

CAATCTATCA ATTACAGTCC GTCCACCACC                                    1750

( 2 ) INFORMATION FOR SEQ ID NO:2:

( i ) SEQUENCE CHARACTERISTICS:
        ( A ) LENGTH: 491 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met<br>1 | Ala | Leu | Phe | Gly<br>5 | Ala | Leu | Phe | Leu | Ala<br>10 | Leu | Leu | Ala | Gly | Ala<br>15 | His |
|---|---|---|---|---|---|---|---|---|---|---|---|---|---|---|---|
| Ala | Glu | Phe | Pro<br>20 | Gly | Cys | Lys | Ile | Arg<br>25 | Val | Thr | Ser | Lys | Ala<br>30 | Leu | Glu |
| Leu | Val | Lys<br>35 | Gln | Glu | Gly | Leu | Arg<br>40 | Phe | Leu | Glu | Gln | Glu<br>45 | Leu | Glu | Thr |
| Ile | Thr<br>50 | Ile | Pro | Asp | Leu | Arg<br>55 | Gly | Lys | Glu | Gly | His<br>60 | Phe | Tyr | Tyr | Asn |
| Ile<br>65 | Ser | Glu | Val | Lys | Val<br>70 | Thr | Glu | Leu | Gln | Leu<br>75 | Thr | Ser | Ser | Glu | Leu<br>80 |
| Asp | Phe | Gln | Pro | Gln<br>85 | Gln | Glu | Leu | Met | Leu<br>90 | Gln | Ile | Thr | Asn | Ala<br>95 | Ser |
| Leu | Gly | Leu | Arg<br>100 | Phe | Arg | Arg | Gln | Leu<br>105 | Leu | Tyr | Trp | Phe | Phe<br>110 | Tyr | Asp |
| Gly | Gly | Tyr<br>115 | Ile | Asn | Ala | Ser | Ala<br>120 | Glu | Gly | Val | Ser | Ile<br>125 | Arg | Thr | Gly |
| Leu | Glu<br>130 | Leu | Ser | Arg | Asp | Pro<br>135 | Ala | Gly | Arg | Met | Lys<br>140 | Val | Ser | Asn | Val |
| Ser<br>145 | Cys | Gln | Ala | Ser | Val<br>150 | Ser | Arg | Met | His | Ala<br>155 | Ala | Phe | Gly | Gly | Thr<br>160 |
| Phe | Lys | Lys | Val | Tyr<br>165 | Asp | Phe | Leu | Ser | Thr<br>170 | Phe | Ile | Thr | Ser | Gly<br>175 | Met |
| Arg | Phe | Leu | Leu<br>180 | Asn | Gln | Gln | Ile | Cys<br>185 | Pro | Val | Leu | Tyr | His<br>190 | Ala | Gly |
| Thr | Val | Leu<br>195 | Leu | Asn | Ser | Leu | Leu<br>200 | Asp | Thr | Val | Pro | Val<br>205 | Arg | Ser | Ser |
| Val | Asp<br>210 | Glu | Leu | Val | Gly | Ile<br>215 | Asp | Tyr | Ser | Leu | Met<br>220 | Lys | Asp | Pro | Val |
| Ala<br>225 | Ser | Thr | Ser | Asn | Leu<br>230 | Asp | Met | Asp | Phe | Arg<br>235 | Gly | Ala | Phe | Phe | Pro<br>240 |
| Leu | Thr | Glu | Arg | Asn<br>245 | Trp | Ser | Leu | Pro | Asn<br>250 | Arg | Ala | Val | Glu | Pro<br>255 | Gln |
| Leu | Gln | Glu | Glu<br>260 | Glu | Arg | Met | Val | Tyr<br>265 | Val | Ala | Phe | Ser | Glu<br>270 | Phe | Phe |
| Phe | Asp | Ser<br>275 | Ala | Met | Glu | Ser | Tyr<br>280 | Phe | Arg | Ala | Gly | Ala<br>285 | Leu | Gln | Leu |
| Leu | Leu<br>290 | Val | Gly | Asp | Lys | Val<br>295 | Pro | His | Asp | Leu | Asp<br>300 | Met | Leu | Leu | Arg |
| Ala<br>305 | Thr | Tyr | Phe | Gly | Ser<br>310 | Ile | Val | Leu | Leu | Ser<br>315 | Pro | Ala | Val | Ile | Asp<br>320 |
| Ser | Pro | Leu | Lys | Leu<br>325 | Glu | Leu | Arg | Val | Leu<br>330 | Ala | Pro | Pro | Arg | Cys<br>335 | Thr |
| Ile | Lys | Pro | Ser<br>340 | Gly | Thr | Thr | Ile | Ser<br>345 | Val | Thr | Ala | Ser | Val<br>350 | Thr | Ile |
| Ala | Leu | Val<br>355 | Pro | Pro | Asp | Gln | Pro<br>360 | Glu | Val | Gln | Leu | Ser<br>365 | Ser | Met | Thr |
| Met | Asp<br>370 | Ala | Arg | Leu | Ser | Ala<br>375 | Lys | Met | Ala | Leu | Arg<br>380 | Gly | Lys | Ala | Leu |
| Arg<br>385 | Thr | Gln | Leu | Asp | Leu<br>390 | Arg | Arg | Phe | Arg | Ile<br>395 | Tyr | Ser | Asn | His | Ser<br>400 |
| Ala | Leu | Glu | Ser | Leu<br>405 | Ala | Leu | Ile | Pro | Leu<br>410 | Gln | Ala | Pro | Leu | Lys<br>415 | Thr |

|     |     |     |             |     |     |     |     |             |     |     |             |     |     |     |
|-----|-----|-----|-------------|-----|-----|-----|-----|-------------|-----|-----|-------------|-----|-----|-----|
| Met | Leu | Gln | Ile<br>420 | Gly | Val | Met | Pro | Met<br>425 | Leu | Asn | Glu | Arg | Thr<br>430 | Trp | Arg |
| Gly | Val | Gln | Ile<br>435 | Pro | Leu | Pro | Glu<br>440 | Gly | Ile | Asn | Phe<br>445 | Val | His | Glu | Val |
| Val | Thr | Asn | His<br>450 | Ala | Gly | Phe<br>455 | Leu | Thr | Ile | Gly | Ala<br>460 | Asp | Leu | His | Phe |
| Ala<br>465 | Lys | Gly | Leu | Arg | Glu<br>470 | Val | Ile | Glu | Lys | Asn<br>475 | Arg | Pro | Ala | Asp | Val<br>480 |
| Arg | Ala | Ser | Thr | Ala<br>485 | Pro | Thr | Pro | Ser | Thr<br>490 | Ala |     |     |     |     |     |

( 2 ) INFORMATION FOR SEQ ID NO:3:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC6086

( x i ) SEQUENCE DESCRIPTION: SEQ ID NO:3:

ACCGGATCCA ARGTNTAYGA YTTYCTNTCN AC      32

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC6087

( x i ) SEQUENCE DESCRIPTION: SEQ ID NO:4:

ACGGAATTCR TGYTGRTTNA GNARRAA      27

( 2 ) INFORMATION FOR SEQ ID NO:5:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC3169

( x i ) SEQUENCE DESCRIPTION: SEQ ID NO:5:

AATTCGAGCT C      11

( 2 ) INFORMATION FOR SEQ ID NO:6:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC3168

( x i ) SEQUENCE DESCRIPTION: SEQ ID NO:6:

AATTGAGCTC G      11

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (vii) IMMEDIATE SOURCE:
        (B) CLONE: ZC1773

(xi) SEQUENCE DESCRIPTION: SEQ ID NO:7:

```
AATTAGGGAG ACCGGAATTC TGTGCTCTGT CAA                    33
```

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (vii) IMMEDIATE SOURCE:
        (B) CLONE: ZC1774

(xi) SEQUENCE DESCRIPTION: SEQ ID NO:8:

```
AATTTTGACA GAGCACAGAA TTCCGGTCTC CCT                    33
```

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (vii) IMMEDIATE SOURCE:
        (B) CLONE: ZC6203

(xi) SEQUENCE DESCRIPTION: SEQ ID NO:9:

```
AAAGCGCATC CCTGAGGTGA TGAAC                             25
```